(12) United States Patent
Rothaemel et al.

(10) Patent No.: US 8,524,970 B2
(45) Date of Patent: Sep. 3, 2013

(54) PROCESS AND PLANT FOR PRODUCING SYNTHETIC FUELS

(75) Inventors: Martin Rothaemel, Frankfurt am Main (DE); Uwe Fincke, Kjorsvikbugen (NO); Holger Dropsch, Nidderau (DE); Henning Buchold, Hanau (DE)

(73) Assignee: Lurgi GmbH, Frankfurt am Main (DE)

( * ) Notice: Subject to any disclaimer, the term of this patent is extended or adjusted under 35 U.S.C. 154(b) by 804 days.

(21) Appl. No.: 12/599,554

(22) PCT Filed: Apr. 29, 2008

(86) PCT No.: PCT/EP2008/003442
§ 371 (c)(1),
(2), (4) Date: Nov. 10, 2009

(87) PCT Pub. No.: WO2008/138479
PCT Pub. Date: Nov. 20, 2008

(65) Prior Publication Data
US 2010/0305376 A1 Dec. 2, 2010

(30) Foreign Application Priority Data

May 11, 2007 (DE) .......................... 10 2007 022 175

(51) Int. Cl.
| | |
|---|---|
| *C07C 1/00* | (2006.01) |
| *C07C 2/00* | (2006.01) |
| *C07C 4/00* | (2006.01) |
| *C07C 5/00* | (2006.01) |
| *C07C 6/00* | (2006.01) |
| *C10G 51/02* | (2006.01) |
| *C10G 55/02* | (2006.01) |
| *C10B 57/02* | (2006.01) |

(52) U.S. Cl.
USPC ........... 585/639; 585/640; 585/310; 585/315; 208/49

(58) Field of Classification Search
USPC .................... 585/639, 640, 310, 315; 208/49
See application file for complete search history.

(56) References Cited

U.S. PATENT DOCUMENTS 4,025,575 A * 5/1977 Chang et al. .................. 585/640
4,482,772 A * 11/1984 Tabak ............................ 585/254

(Continued)

FOREIGN PATENT DOCUMENTS

| DE | 102005003109 A1 | 7/2006 |
| EP | 1410844 | 4/2004 |
| WO | WO-2006/076942 | 7/2006 |

OTHER PUBLICATIONS

International Search Report and Written Opinion, dated Aug. 1, 2008 (12 pages).

*Primary Examiner* — Patricia L Hailey
(74) *Attorney, Agent, or Firm* — Pauly, Devries, Smith & Deffner, L.L.C.

(57) ABSTRACT

In a process for producing synthetic fuels from an educt mixture containing hydrogen and oxygenates, such as methanol and/or dimethyl ether, the educt mixture is reacted on a catalyst in a first process stage to obtain a hydrocarbon product containing olefins with preferably 2 to 8 carbon atoms. In a second process stage the hydrocarbon product is oligomerized to long-chain olefins, from which gasoline and Diesel products are obtained. The hydrocarbon product obtained in the first process stage is separated into a liquid phase and a gaseous phase. The gaseous phase is supplied to the second process stage. The liquid phase is separated into a mixture rich in $C_{6-}$ hydrocarbons and a mixture containing $C_{7+}$ hydrocarbons and aromatics. The mixture rich in $C_{6-}$ hydrocarbons is supplied to the second process stage. The mixture containing $C_{7+}$ hydrocarbons −+ and aromatics can be admixed to the gasoline product for quality improvement.

14 Claims, 2 Drawing Sheets

(56) References Cited

U.S. PATENT DOCUMENTS

| | | | |
|---|---|---|---|
| 4,579,999 A * | 4/1986 | Gould et al. | 585/312 |
| 4,689,205 A * | 8/1987 | Gould et al. | 422/142 |
| 4,709,113 A * | 11/1987 | Harandi et al. | 585/640 |
| 4,851,606 A * | 7/1989 | Ragonese et al. | 585/640 |
| 4,899,002 A * | 2/1990 | Harandi et al. | 585/312 |
| 4,929,780 A * | 5/1990 | Wright et al. | 585/303 |
| 5,177,279 A * | 1/1993 | Harandi | 585/312 |
| 6,049,017 A * | 4/2000 | Vora et al. | 585/324 |
| 6,875,899 B2 * | 4/2005 | Martens et al. | 585/327 |
| 7,495,141 B2 * | 2/2009 | Lumgair et al. | 585/639 |
| 7,663,012 B2 * | 2/2010 | Kalnes et al. | 585/640 |
| 7,678,953 B2 * | 3/2010 | Kuechler et al. | 585/502 |
| 7,945,141 B2 * | 5/2011 | Jung et al. | 386/240 |
| 2002/0103406 A1 | 8/2002 | Mathys et al. | |
| 2008/0039670 A1 * | 2/2008 | Miller et al. | 585/639 |
| 2009/0005624 A1 * | 1/2009 | Bozzano | 585/639 |
| 2012/0102829 A1 * | 5/2012 | Rothaemel et al. | 44/447 |

\* cited by examiner

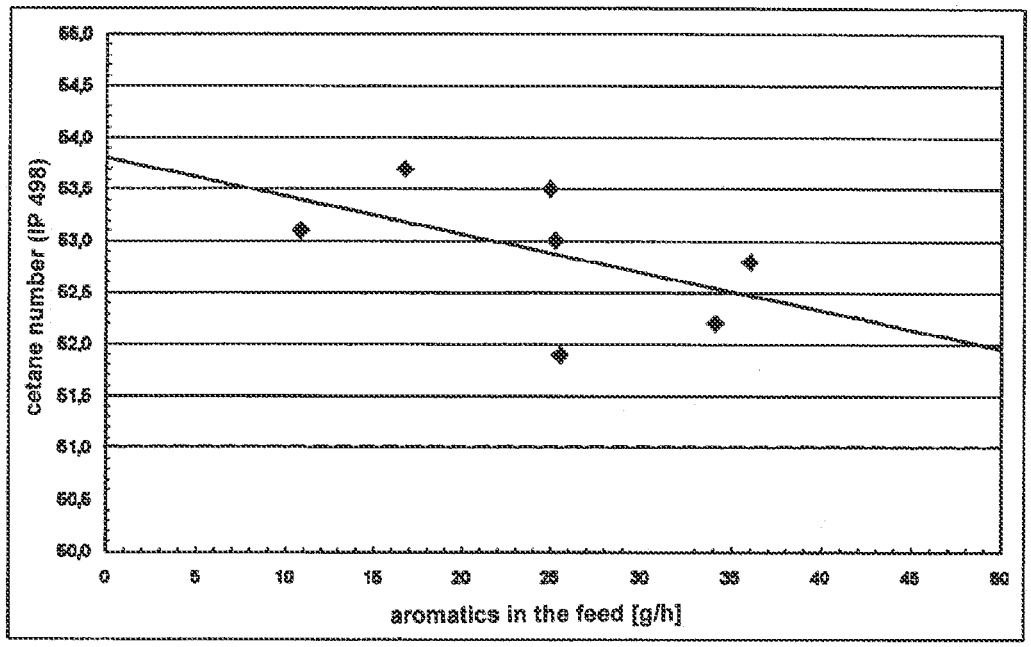
Fig. 2.1: Dependence of the measured cetane numbers (IP 498) of the Diesel product upon hydrogenation on the aromatics mass flow in the feed of the oligomerization reactor
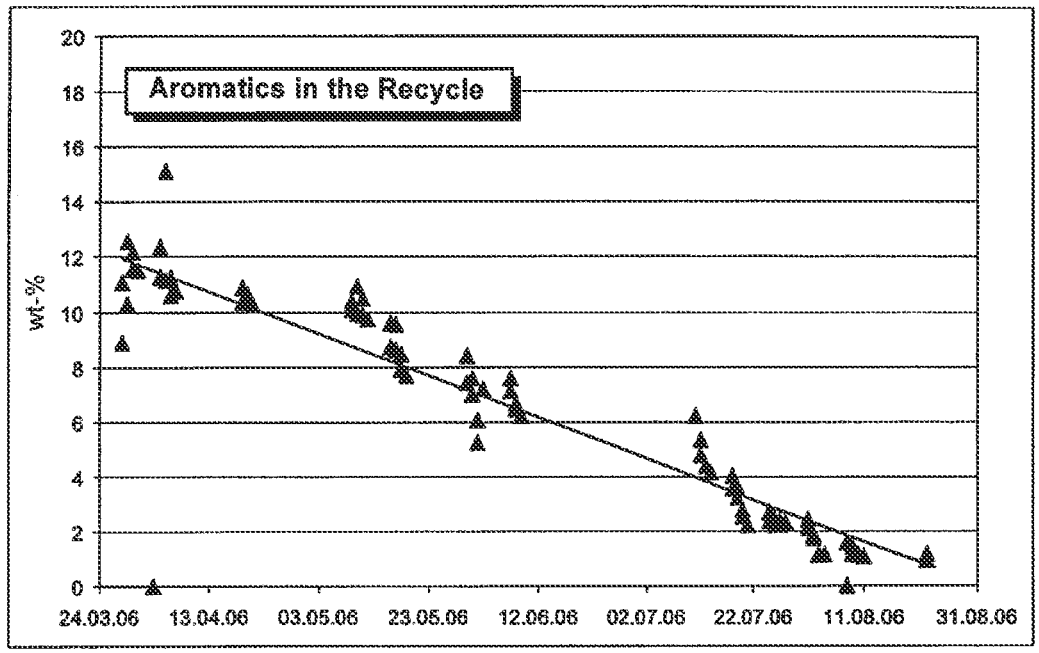
Fig. 2.2: Decrease of the aromatics content with time in the recycle of the oligomerization reactor

US 8,524,970 B2

PROCESS AND PLANT FOR PRODUCING SYNTHETIC FUELS

CROSS-REFERENCE TO RELATED APPLICATIONS

This application is a national stage application under 35 U.S.C. 371 of International Patent Application Serial No. PCT/EP2008/003442, entitled "Verfahren und Anlage zur Herstellung von synthetischen Kraftstoffen," filed Apr. 29, 2008, which claims priority from German Patent Application No. 10 2007 022 175.6, filed May 11, 2007.

FIELD OF THE INVENTION

The present invention relates to a process and a plant for producing synthetic fuels from an educt mixture containing steam and oxygenates, such as methanol and/or dimethyl ether (DME), in which in a first process stage the educt mixture is reacted on a catalyst to obtain a hydrocarbon product containing olefins with preferably 2 to 8 carbon atoms, and in a second process stage the hydrocarbon product obtained is oligomerized to higher olefins with mostly more than 5, preferably 10 to 20 carbon atoms.

BACKGROUND OF THE INVENTION

Such process for producing synthetic fuels (so-called MtSynfuels process; MtSynfuels=Methanol to synthetic fuels) is known from WO 2006/076942 A1. In an olefin reactor, a mixture consisting of oxygenates, such as methanol and/or DME, and steam initially is reacted on a zeolite catalyst to obtain short-chain olefins. As by-products, paraffins and aromatics are obtained. Subsequent to the olefin production, the olefin mixture obtained in the olefin reactor is densified, partly condensed, and in a second process stage the condensate is oligomerized to long-chain hydrocarbons. In the process, the aromatics are alkylated. In a succeeding separating means, the oligomerized product stream is divided into a product stream containing synthetic fuels (LPG, gasoline, heating gas and, upon hydrogenation, Diesel/Kerojet) and streams containing unsaturated and saturated hydrocarbons, respectively. The saturated hydrocarbons are recirculated to the olefin reactor, whereas the unsaturated hydrocarbons are recycled to the oligomerization reactor.

In the conventional MtSynfuels process, the olefin reaction usually is performed at a low pressure of 1 to 2 bar. This requires large apparatuses and machines and therefore leads to high investment costs.

The alkylation of the aromatics in the oligomerization reactor leads to a reduction of the cetane number achievable in the Diesel, as the cycloalkanes obtained therefrom in the succeeding hydrogenation have low cetane numbers. A cetane number which is too low can lead to an ignition delay between the injection and the self-ignition of the fuel, and hence to an abrupt, explosion-like combustion of fuel with a loud combustion noise.

SUMMARY OF THE INVENTION

Therefore, it is the object of the invention to improve the quality of the synthetic fuels produced.

This object substantially is solved with the invention by a process with the features of claim 1 in that before introduction into the second process stage the hydrocarbon product obtained in the first process stage is separated into a liquid and a gaseous phase, that the gaseous phase of the hydrocarbon product is supplied to the second process stage, that in a second separating means the liquid phase of the hydrocarbon product is separated into a mixture rich in $C_{6-}$ hydrocarbons and a mixture containing $C_{7+}$ hydrocarbons and aromatics, and that the mixture rich in $C_{6-}$ hydrocarbons is supplied to the second process stage. By discharging aromatics prior to oligomerization, the amount of cycloalkanes obtained during hydrogenation can be reduced and the cetane number of the Diesel product can be increased thereby.

In accordance with a preferred aspect of the invention, the production of olefins in the first process stage is performed at a pressure of more than 2 bar, preferably 2 to 10 bar, in particular 3 to 8 bar. By increasing the pressure of the olefin reaction, the cross-section of the olefin reactor and of the apparatuses and fittings connected thereto (heat exchangers, valves, pipe conduits) can distinctly be reduced. This leads to a corresponding reduction of the investment costs.

In accordance with a development of the invention, the gasoline fraction is separated from the gaseous phase of the hydrocarbon product before introduction into the second process stage and supplied to the gasoline product stream. This improves the quality of the gasoline product.

In accordance with a preferred embodiment of the invention, the separation of the liquid phase of the hydrocarbon product is effected by distillation after the first process stage, wherein the top product of the distillation, which is the mixture rich in $C_{6-}$ hydrocarbons, is supplied to the second process stage in accordance with the invention.

With the bottom product of the distillation, the mixture containing $C_{7+}$ hydrocarbons and aromatics is obtained, which in accordance with a development of the invention is added to a gasoline product stream separated after the oligomerization reactor.

If a Diesel product stream is separated from the hydrocarbon product obtained in the second process stage, the bottom product of the distillation is added to the Diesel product stream upon hydrogenation in accordance with a development of the invention.

If a gasoline product stream is separated from the hydrocarbon product obtained in the second process stage, the product obtained from the top distillate and/or at least one side outlet of the distillation is supplied to the gasoline product stream in accordance with the invention.

This invention also relates to a plant for producing synthetic fuels from an educt mixture containing steam and oxygenates, such as methanol and/or DME, which can be used in particular for performing the process of the invention. The plant comprises at least one catalytic olefin reactor for converting the educt mixture to a hydrocarbon product containing olefins with preferably 2 to 8 carbon atoms and at least one oligomerization reactor downstream of the olefin reactor for converting the hydrocarbon product obtained to long-chain hydrocarbons, a first separating means for separating the hydrocarbon product obtained in the olefin reactor into a gaseous phase and a liquid phase, and a second separating means for separating the liquid phase of the hydrocarbon product into a mixture rich in $C_{6-}$ hydrocarbons and a mixture containing $C_{7+}$ hydrocarbons and aromatics.

In accordance with the invention, the second separating means is a distillation column, whose top region is connected with the inlet of the oligomerization reactor.

Developments, advantages and possible applications of the invention can also be taken from the following description of embodiments and the drawing. All features described and/or illustrated in the drawing form the subject-matter of the invention per se or in any combination, independent of their inclusion in the claims or their back-reference.

DETAILED DESCRIPTION

Figure 1:
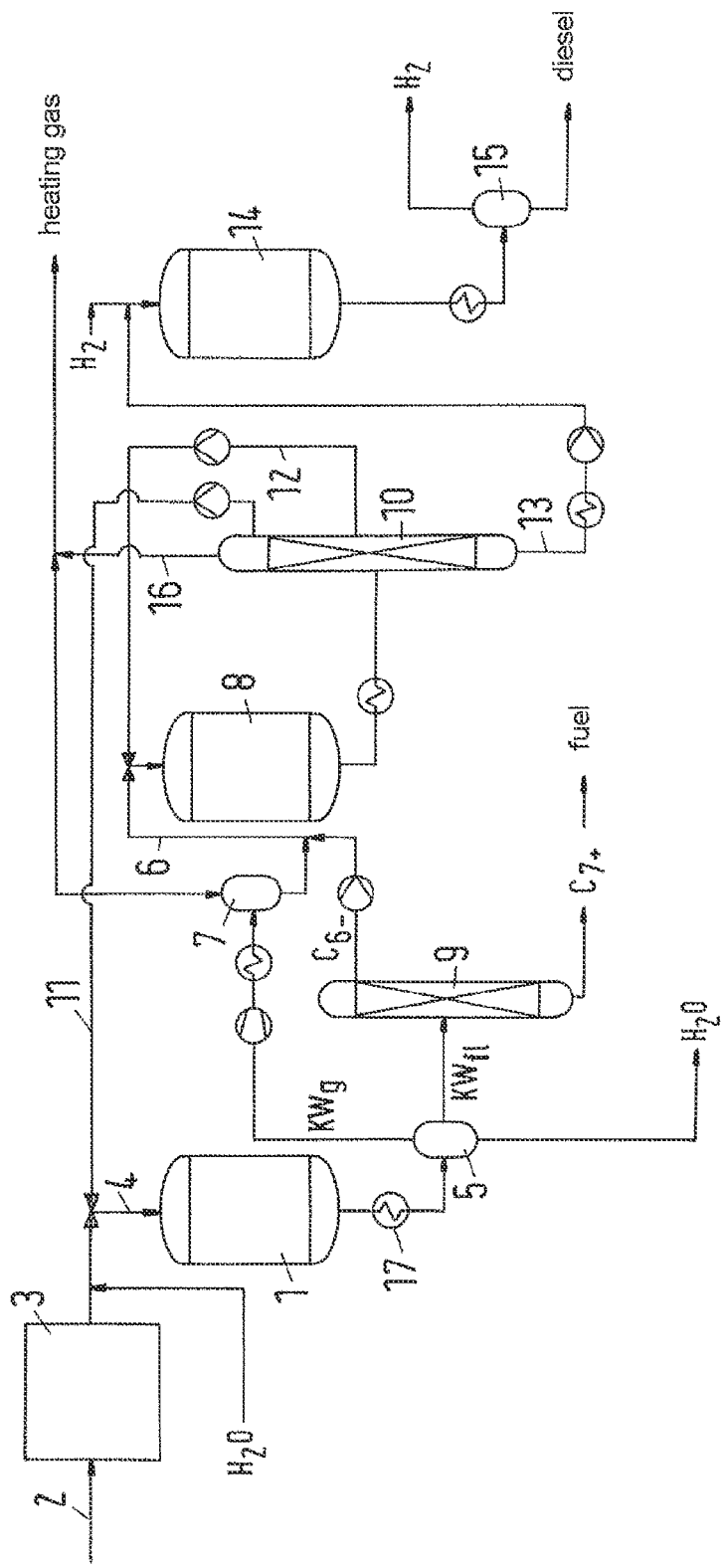
FIG. 1 schematically shows a plant suitable for performing the process of the invention, FIG. 2.1 shows the dependence of the measured cetane numbers (IP 498) of the Diesel product upon hydrogenation on the aromatics mass flow in the feed of the oligomerization reactor and FIG. 2.2 shows the decrease of the aromatics content with time in the recycle of the oligomerization reactor.

The plant illustrated in FIG. 1 first of all comprises an olefin reactor 1, which contains a catalyst on the basis of form-selective zeolite, preferably an aluminum silicate zeolite of the pentasil type, and particularly preferably ZSM-5, or catalysts based on silicalite or aluminum phosphate (SAPO). The olefin reactor 1 preferably is a multistage adiabatic fixed-bed reactor, but it is also possible to merely use a single-stage reactor or several reactors arranged in parallel or in series.

In operation of the plant, methanol supplied via a methanol supply conduit 2 is heated in a non-illustrated heat exchanger to a temperature of preferably 200 to 350° C. and evaporated thereby, before the methanol vapor is at least partly converted to dimethyl ether and water in a DME reactor 3 on a suitable dehydrogenation catalyst, for instance alumina. The methanol/dimethyl ether mixture withdrawn from the DME reactor 3 is supplied to the olefin reactor 1 via a conduit 4. Initially, a partial stream of the educt mixture can be branched off via a branch conduit (not shown) and upon cooling be charged in individual partial streams in the form of gas to the individual reactor stages of the multistage olefin reactor 1. The main stream is charged to the first stage of the olefin reactor 1. Preferably, the inlet temperature into the first stage of the olefin reactor 1 is between 350 and 500° C. The weight ratio of water to methanol equivalent in the educt mixture preferably lies between 0.25:1 and 10:1. According to the equation 2 $CH_3OH \rightarrow CH_3-O-CH_3+H_2O$, one "methanol equivalent" here corresponds to half a mole of dimethyl ether. Methanol or dimethyl ether in combination with steam can exclusively be used as educt in the reactor 1 instead of the steam/methanol/dimethyl ether mixture.

The olefin reactor 1 is operated with an elevated pressure >2 bar, preferably 2 to 10 bar, in particular 3 to 8 bar. In the catalyst region of the olefin reactor 1, the temperatures preferably lie between 300 and 600° C.

When the olefin reactor is operated at a lower pressure, the reaction mixture formed in the olefin reactor chiefly consists of $C_2$-$C_4$ olefins, $C_{5+}$ gasoline hydrocarbons and steam. By increasing the pressure in the olefin reactor 1 to >2 bar, the product spectrum is shifted towards long-chain olefins and paraffins (up to about $C_8$) and to a smaller extent towards aromatics.

Subsequent to the olefin reactor 1, and upon cooling via a heat exchanger 17, the reaction mixture obtained is separated in a first separating means 5 (3-phase separator) into an aqueous phase, a gaseous hydrocarbon stream $HC_g$ and a liquid hydrocarbon stream $HC_{liq}$. Part of the aqueous phase can be recirculated to the inlet of the olefin reactor 1.

Upon densification and partial condensation, possibly upon separation of a fraction of gaseous hydrocarbons in a separating means 7, the gaseous hydrocarbons are supplied to the inlet of an oligomerization reactor 8 via a conduit 6.

The liquid hydrocarbons obtained in the first separating means 5 are supplied to a second separating means 9 in the form of a distillation column, in which they are separated into a $C_{6-}$ hydrocarbon stream and a mixture containing $C_{7+}$ hydrocarbon and aromatics. At the top of the distillation column 9, the $C_{6-}$ hydrocarbon stream is withdrawn and supplied to the inlet of the multistage oligomerization reactor 8. The mixture of $C_{7+}$ hydrocarbons and aromatics is withdrawn and can be supplied to a gasoline product stream.

The hydrocarbon mixture supplied to the first stage of the multistage oligomerization reactor 8 is oligomerized in the same at temperatures between 200 and 450° C. and at a pressure of 40 to 100 bar in the presence of zeolite catalysts of the pentasil type. The olefins obtained by oligomerization mostly have more than 5, preferably between 10 and 20 carbon atoms. The mixture obtained is processed in a succeeding distillation column 10 (third separating means), wherein a distillate is separated, which forms the Diesel product upon hydrogenation. Furthermore, there are provided two hydrocarbon streams of different composition. A hydrocarbon stream rich in paraffins is recirculated to the olefin reactor 1 via a conduit 11, whereas a stream rich in olefins is returned to the inlet region of the oligomerization reactor 8 via a conduit 12. From the hydrocarbon streams rich in olefins and in paraffins, partial quantities can be withdrawn for providing the gasoline product. After admixing hydrogen, the liquid product withdrawn from the bottom of the distillation column 10 via the conduit 13 is supplied to a hydrogenation plant 14, in which the unsaturated hydrocarbons are converted into Diesel. In a succeeding separating means 15, the Diesel products are separated from excess hydrogen. The most part of the excess hydrogen can be recycled to the hydrogenation reactor 14.

At the top of the third separating means 10, a heating gas stream is withdrawn via a conduit 16, and depending on the configuration of the third separating means 10, further product streams such as LPG or gasoline can also be withdrawn.

Due to the separation of the $C_{7+}$ components in the second separating means, the yield of Diesel fuel actually is reduced. This effect is overcompensated, however, by the increase of the gasoline yield and in particular the increase of the quality both of the gasoline and of the Diesel product, for which higher octane or cetane numbers are obtained. By discharging the aromatics in the second separating means, the cetane number in the Diesel product is increased. Since the aromatics discharged are instead added to the gasoline product, the octane number thereof is increased at the same time.

EXAMPLES

Example 1

Increase of the Cetane Numbers of the Diesel Product by Separating the $C_{7+}$ Hydrocarbons from the Feed of the Oligomerization Reactor As compared to non-aromatic hydrocarbons of the same carbon number, aromatic hydrocarbons have a considerably smaller cetane number. Numerical examples to illustrate this effect are listed below in Table 1.1.

TABLE 1.1

Cetane numbers (CN) for aromatic and non-aromatic hydrocarbons (HC) of the same carbon number.

| C number | Aromatic HC/CN | | Non-aromatic HC/CN | |
| --- | --- | --- | --- | --- |
| 6 | benzene | 0 | n-hexane | 42 . . . 45 |
| 12 | n-hexyl benzene | 26 | n-dodecane | 80 . . . 88 |
| 16 | n-octyl xylene | 20 | n-hexadecane (cetane, by definition) | 100 |

(Source: Murphy, M. J. et al., Compendium of Experimental Cetane Number Data, National Renewable Energy Laboratory (www.nrel.gov), NREL/SR-540-36805, September 2004)

A rather complete removal of aromatic hydrocarbons both from fresh feed and from the HC recycle recirculated to the oligomerization reactor therefore is of great importance for increasing the cetane number of the Diesel product.

FIG. 2.1 graphically illustrates the relationship between the aromatics mass flow in the feed of the oligomerization reactor and the measured cetane numbers of the Diesel product upon hydrogenation. By means of distillative separation and discharge of the $C_{7+}$ cut from the feed of the oligomerization reactor, an immediate decrease of the aromatics mass flow in the fresh feed and a continuous decrease in the recycle of the oligomerization reactor except for trace amounts could be achieved, see FIG. 2.2.

Example 2

Octane Numbers of the Gasoline Product Streams

Before starting the aromatics column, the liquid hydrocarbon streams withdrawn via conduit 11 at the top of the column and via conduit 12 at a side outlet of the Diesel column 10 have formed the gasoline product. After starting the distillative separation of the liquid hydrocarbon product from the olefin reactor 1, a further partial stream rich in aromatics with a high octane number is available for the gasoline product. Typical octane numbers of the three partial streams are listed in the following Table 2.1.

TABLE 2.1

Important properties of the partial streams of the gasoline product

| Partial Stream | Octane Number (RON) |
|---|---|
| Top distillate (11) | 81.4 |
| Side outlet (12) | 83.0 |
| Bottom of aromatics column ($C_{7+}$) | 96.4 |

According to DIN EN 228 applicable for Otto fuels, the aromatics content is limited to 42 vol-%, with a limit value of 1 vol-% being applicable for the benzene content ($C_6H_6$). As shown in Table 2.2, the bottom of the aromatics column ($C_{7+}$) virtually is free from benzene. It can therefore be added to the gasoline product, until the limit value for the total aromatics content is reached.

TABLE 2.2

Typical distribution of aromatic hydrocarbons in the bottom of the aromatics column ($C_{7+}$)

| | Carbon Number | | | | | | | |
|---|---|---|---|---|---|---|---|---|
| | 6 | 7 | 8 | 9 | 10 | 11 | 12 | Total |
| Wt-% | 0.0 | 4.7 | 34.9 | 27.9 | 7.6 | 0.5 | 0.0 | 75.5 |

Example 3

Change in Quantity of the Diesel and Gasoline Products by Separating the $C_{7+}$ Hydrocarbons from the Feed of the Oligomerization Reactor By distillative separation and discharge of the $C_{7+}$ cut from the liquid hydrocarbon product of the olefin reactor 1, the quantity of the total feed supplied to the oligomerization reactor 8 is reduced. Since this cut is added to the gasoline product, its quantity is increased correspondingly. Typical product quantities with and without fractionation of the olefin reactor liquid product are compared below in Table 3.1.

Based on 1000 g/h fresh feed, 622 g/h Diesel product are obtained without fractionation, and 616 g/h in the case with fractionation. Consequently, the influence of the fractionation on the Diesel yield is comparatively small. On the other hand, the gasoline quantity is increased from 188 g/h (without fractionation) to 292 g/h (with fractionation) per 1000 g/h fresh feed.

TABLE 3.1

Typical feed and product quantities of the oligomerization reactor without and with fractionation of the liquid hydrocarbon product from the olefin reactor

| Stream Designation | Without Fractionation Mass Flow/g/h | With Fractionation Mass Flow/g/h |
|---|---|---|
| Feed Streams | | |
| Fresh feed [#] | 308 | 229 |
| Recycle | 903 | 926 |
| Product Streams | | |
| Bottom of aromatics column ($C_{7+}$) | 0 | 32 |
| Top gas (16) | 43 | 46 |
| Top distillate (11) + side outlet (12) | 961 | 961 |
| Gasoline purge | 58 | 35 |
| Bottom of Diesel column (13) | 192 | 141 |

[#] Fresh feed to the oligomerization reactor = gaseous product of the olefin reactor + top product of the aromatics column

LIST OF REFERENCE NUMERALS

| 1 | olefin reactor |
|---|---|
| 2 | methanol supply conduit |
| 3 | DME reactor |
| 4 | conduit |
| 5 | first separating means |
| 6 | conduit |
| 7 | separating means |
| 8 | oligomerization reactor |
| 9 | second separating means |
| 10 | third separating means |
| 11 | conduit |
| 12 | conduit |
| 13 | conduit |
| 14 | hydrogenation plant |
| 15 | separating means |
| 16 | conduit |
| 17 | heat exchanger |
| $HC_g$ | gaseous hydrocarbon stream |
| $HC_{liq}$ | liquid hydrocarbon stream |

The invention claimed is:

1. A process for producing synthetic fuels from an educt mixture containing steam and oxygenates comprising:
   a first process stage, in which the educt mixture is reacted on a catalyst to obtain a hydrocarbon product containing olefins with 2 to 8 carbon atoms,
   a second process stage, in which the hydrocarbon product obtained is oligomerized to higher olefins with 10 to 20 carbon atoms, and
   a third process stage, in which a product stream from the second process stage is separated into three streams: a distillate stream, which is formed into diesel; a hydrocarbon stream rich in paraffins, which is recycled to the first process stage; and a hydrocarbon stream rich in olefins, which is recycled to the second process stage, wherein the hydrocarbon product obtained in the first process stage is separated into a liquid and a gaseous phase before introduction into the second process stage, the gaseous phase of the hydrocarbon product is supplied to the second process stage, the liquid phase of the hydrocarbon product is separated into a mixture rich in $C_{6-}$ hydrocarbons and a mixture containing $C_{7+}$ hydrocarbons and aromatics, and the mixture rich in $C_{6-}$ hydrocarbons is supplied to the second process stage.

2. The process according to claim 1, wherein the generation of olefins is performed in the first process stage at a pressure of more than 2 bar.

3. The process according to claim 1, wherein the mixture containing $C_{7+}$ hydrocarbons and aromatics is at least partly supplied to a gasoline product.

4. The process according to claim 1, wherein the separation of the liquid phase of the hydrocarbon product is effected by distillation after the first process stage.

5. The process according to claim 4, wherein the top product of the distillation is supplied to the second process stage.

6. The process according to claim 4, wherein a Diesel product stream is separated from the hydrocarbon product obtained in the second process stage, wherein upon hydrogenation the bottom product of the distillation is at least partly added to the Diesel product stream.

7. The process according to claim 4, wherein a gasoline product stream is separated from the hydrocarbon product obtained in the second process stage, and wherein the product obtained from the top distillate and/or a side outlet of the distillation is at least partly added to the gasoline product stream.

8. The process according to claim 1, wherein the educt mixture comprises methanol and/or dimethyl ether.

9. The process according to claim 1, wherein the generation of olefins is performed in the first processing stage at a pressure of 2 to 10 bar.

10. The process according to claim 1, wherein the generation of olefins is performed in the first process stage at a pressure of 3 to 8 bar.

11. A plant for producing synthetic fuels from an educt mixture containing steam and oxygenates, comprising at least one catalytic olefin reactor for converting the educt mixture to a hydrocarbon product containing olefins with 2 to 8 carbon atoms, at least one oligomerization reactor downstream of the olefin reactor for converting the hydrocarbon product obtained to long-chain hydrocarbons, and a separating device for fractionating a product stream from the oligomerization reactor into three streams: a distillate stream, which is formed into diesel; a hydrocarbon stream rich in paraffins, which is recycled to the catalytic olefin reactor; and a hydrocarbon stream rich in olefins, which is recycled to the oligomerization reactor, a first separating means for separating the hydrocarbon product obtained in the olefin reactor into a gaseous phase and a liquid phase, and a second separating means for separating the liquid phase of the hydrocarbon product into a mixture rich in $C_{6-}$ hydrocarbons and a mixture containing $C_{7+}$ hydrocarbons and aromatics.

12. The plant according to claim 11, wherein the second separating means is a distillation column.

13. The plant according to claim 11, wherein the top region of the second separating means is connected with the inlet of the oligomerization reactor via a conduit.

14. The plant according to claim 11, wherein the educt mixture comprises methanol and/or dimethyl ether.

* * * * *

UNITED STATES PATENT AND TRADEMARK OFFICE
CERTIFICATE OF CORRECTION

| | | |
|---|---|---|
| PATENT NO. | : 8,524,970 B2 | Page 1 of 1 |
| APPLICATION NO. | : 12/599554 | |
| DATED | : September 3, 2013 | |
| INVENTOR(S) | : Martin Rothaemel et al. | |

It is certified that error appears in the above-identified patent and that said Letters Patent is hereby corrected as shown below:

On the Title page of the U.S. Patent, please change the spelling of the second named inventor from "Uwe Fincke" to --Uwe Finck--.

Signed and Sealed this
Twelfth Day of November, 2013

Teresa Stanek Rea
*Deputy Director of the United States Patent and Trademark Office*